United States Patent [19]

Chatzipetros et al.

[11] 4,425,811

[45] * Jan. 17, 1984

[54] CRYOGENIC PUMP AND AIR SAMPLER

[75] Inventors: Johann Chatzipetros, Frechen; Manfred Helten, Titz-Muntz, both of Fed. Rep. of Germany

[73] Assignee: Kernforschungsanlage Jülich GmbH, Jülich, Fed. Rep. of Germany

[*] Notice: The portion of the term of this patent subsequent to Jul. 6, 1999 has been disclaimed.

[21] Appl. No.: 390,123

[22] Filed: Jun. 18, 1982

Related U.S. Application Data

[63] Continuation of Ser. No. 198,042, Oct. 17, 1980, Pat. No. 4,337,669.

[30] Foreign Application Priority Data

Oct. 19, 1979 [DE] Fed. Rep. of Germany ....... 2942305

[51] Int. Cl.$^3$ .............................................. G01N 1/14
[52] U.S. Cl. .................................. 73/863.11; 62/55.5; 73/864.34
[58] Field of Search ....................... 73/863.11; 62/55.5

[56] References Cited

U.S. PATENT DOCUMENTS 3,579,998  5/1971  Thibault ............................... 62/55.5
4,283,948  8/1981  Longsworth ..................... 73/863.11

OTHER PUBLICATIONS

LUEB et al., Balloon-Borne Low Temperature Air Sampler, Review of Scientific Instruments, vol. 46, No. 6, Jun. 1975, pp. 702-705.
"Vakuumtechnik" Thiemig-Taschenbocher vol. 43 Die Herausgeber, pp. 94-97 and 310-313, Jan. 1972.

*Primary Examiner*—S. Clement Swisher
*Attorney, Agent, or Firm*—Karl F. Ross; Herbert Dubno

[57] ABSTRACT

A sampling unit, especially for stratospheric air sampling when carried aloft by balloon or another vehicle, comprises a liquid coolant reservoir within an evacuated vessel and provided with a cryogenically cooled adsorber for maintaining the vacuum. Nozzles in the vessel wall can be selectively opened and closed to allow samples to be drawn over cooled fingers on which components of the sample are frozen or sublimed. A vacuum gate can be connected to the device for removal of the cold fingers for transfer to a spectrometer.

12 Claims, 10 Drawing Figures

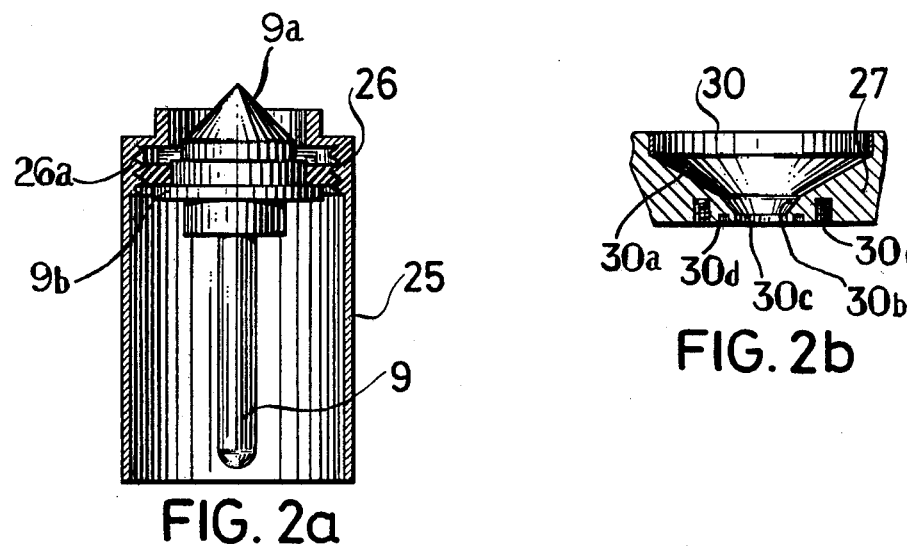
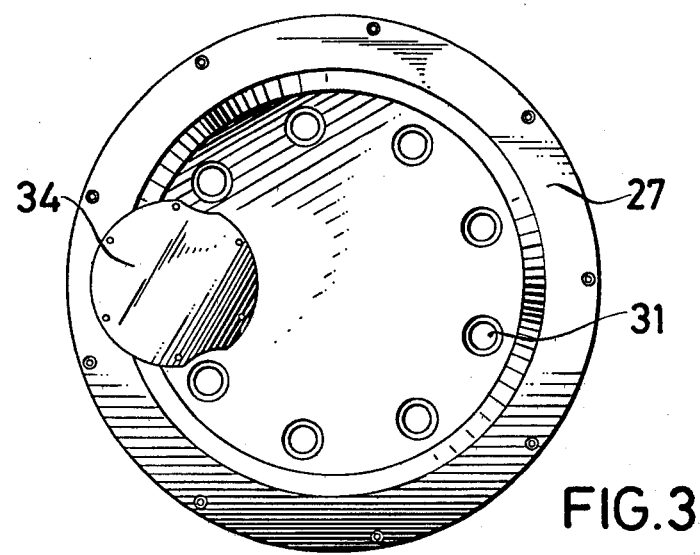

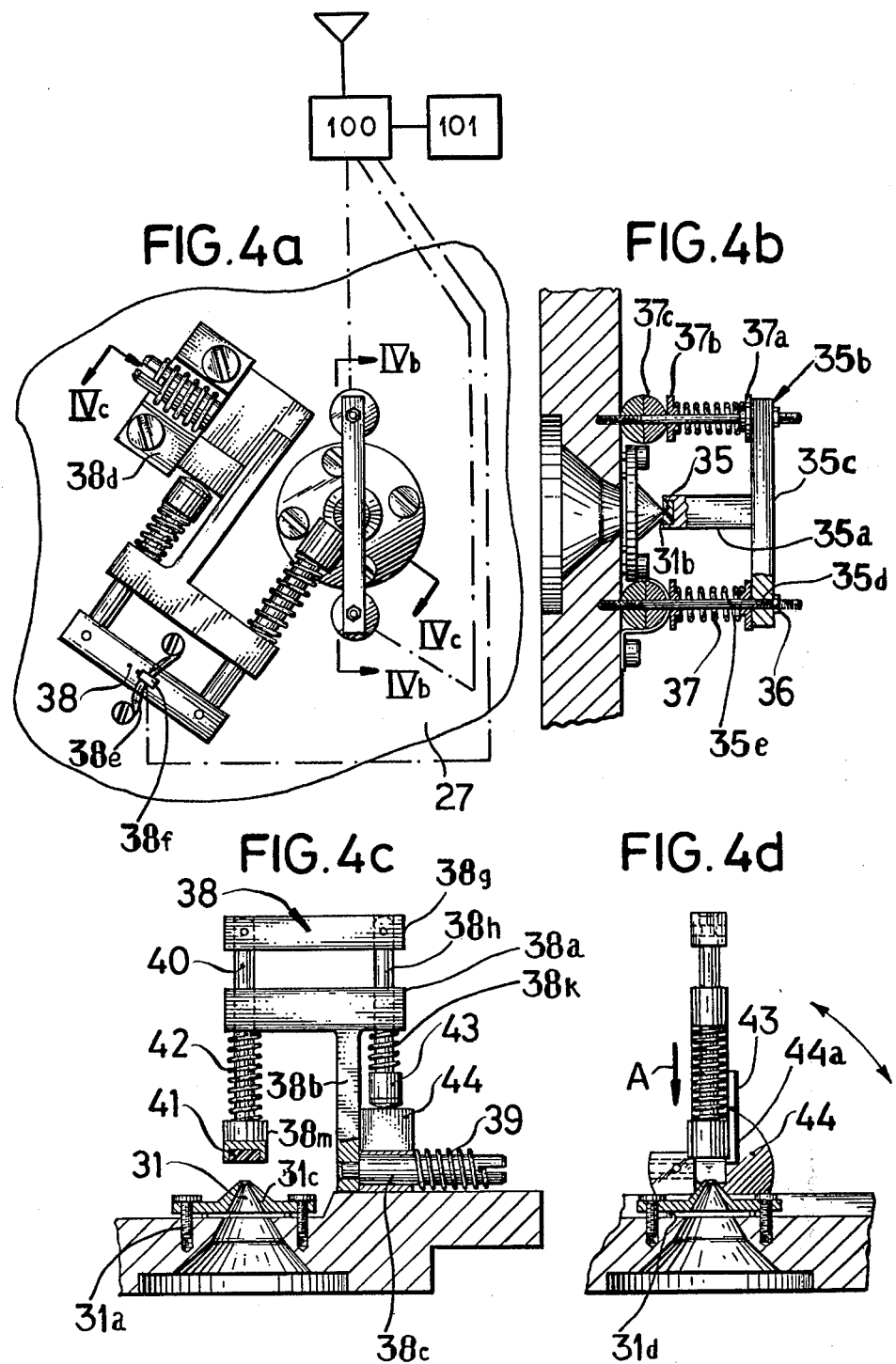

CRYOGENIC PUMP AND AIR SAMPLER

CROSS REFERENCE TO RELATED APPLICATION

This application is a continuation of Ser. No. 198,042 filed Oct. 17, 1980, now U.S. Pat. No. 4,337,669.

FIELD OF THE INVENTION

Our present invention relates to a cryogenic pump and air sampler. More particularly, the invention relates to an air-borne device for the sampling of stratospheric air by cryogenic methods.

BACKGROUND OF THE INVENTION

For determining the chemical and physical characteristics of stratospheric regions and especially for determining the effects of environmental conditions and the activities of mankind on the ozone belt above the earth, it is a common practice to transport, generally by balloon, air sampling devices to appropriate heights and to selectively open communication between the sampling device and the surrounding atmosphere to allow the samples to be collected.

It has been proposed, for the sampling of air at altitudes of 20 to 35 km, to utilize cryogenic samplers in which components of the sample are deposited by freezing or sublimation on a sampling finger or probe which is chilled by a liquid cryogen such as liquid nitrogen.

Samples of this type are effective for determining anthropogenic influences on the atmosphere, e.g. from Freons, fertilizers and the like, the samples being subjected to analysis in ESR spectrometers to determine the content of paramagnetic molecules such as those of $NO_2$ and $HO_2$.

Helium-filled balloons generally carry the sampling devices up to altitudes of 40 km and the sampling can take place over a period of several hours, whereupon the sampling unit is permitted to fall to earth by parachute and is recovered.

A sampling device for the purpose described is discussed in *Ber. Bunsenges. Phys. Chem.*, 82 (1978) pp. 16-19 of D. Mihelcic et al. and utilizes a cryosampler with an evacuated or evacuatable vessel and a remotely controlled inlet nozzle opening when the device reaches the desired altitude. The nozzle is juxtaposed with a cooling finger held at a low temperature by contact with a liquid reservoir. The vacuum vessel is provided with a cryogenically cooled adsorber which maintains the reduced pressure in the vacuum vessel.

When the nozzle orifice is opened at the desired altitude, air is drawn into the vacuum vessel and initially flows along the cooling finger so that any carbon dioxide (which may be present in an amount of 320 parts per million) is frozen out and, in addition, natural and anthropogenic trace gases are collected. Most of the oxygen and nitrogen constituting the air is picked up by the adsorber to maintain the reduced pressure.

The unit, upon completion of its sampling mission, can land at a velocity of about 5 m/sec. and the landing site will vary in terrain from forest, to ravine, to pavement, to mountain or to river, depending upon the geography. Frequently access to the landed unit is difficult and the unit may have to wait 5 to 24 hours before it is recovered and the sample can be removed.

The unit described in this publication has been found to have numerous problems. For example, if the unit lands on its side or in an inverted manner, the liquid coolant is rapidly lost and the sample may likewise be lost. In addition, transfer of the sample to the spectrometer frequently brings the sample into contact with ambient air and reduces the precision of the results. The number of samples which can be taken with the unit is limited.

OBJECTS OF THE INVENTION

It is the principal object of the present invention to provide a lightweight, lowcost cryogenic sampler for the purposes described which has a high degree of reliability and stability, e.g. a weight less than 200 kp (kilogram force), and which will remain operational for long periods of time on landing regardless of the position or orientation thereof.

Another object of the invention is to provide a cryogenic sampler for the recovery of stratospheric air samples and which can be subjected to considerable deceleration forces, i.e. greater than ten times gravitational acceleration, without damage and with critical parts such as the cooling fingers being free from movement or displacement greater than, say, 0.1 mm from an original position, even with impact on landing, all without massive support and mounting structures.

Another object of the invention is to provide a device for the purpose described which can allow residual gases to be pumped out by sorption pump, i.e. a device which can prevent the pressure in the vacuum chamber from substantially exceeding $10^{-3}$ mb, corresponding to an air leakage into the system of 20 standard l/h over a period of four to six hours.

Still another objects of this invention is to provide an apparatus for the cryogenic sampling of air which has capacity for maintaining cooling for up to 24 hours after landing, which has a cooling operation which is independent of orientation or position, and which prevents contamination of the samples on transfer to an ESR spectrometer or the like.

SUMMARY OF THE INVENTION

These objects and others are attained, in accordance with the present invention, in a cryogenic collector in which a generally spherical or ball-shaped liquid reservoir for the liquid cryogen or coolant (such as liquid nitrogen) is mounted in an evacuated vessel and is provided with a partition subdividing this vessel into upper and lower compartments, the latter receiving the adsorber which communicates with the evacuated vessel while the upper compartment is provided with a flexible hose or tube which is weighted and communicates through the membrane with the lower compartment.

The membrane can be provided with a position-dependent valve which closes upon tilting or inversion of the collector to block flow from the second or lower compartment into the first or upper compartment, while a pressure acceleration tube interconnects the two compartments to ensure pressure equalization therebetween. The latter tube terminates approximately at the center of the lower or second compartment.

According to the invention, moreover, the flexible tube runs to a heat exchange surface of annular form provided at the base of the adsorber and from which a plurality of conductively-cooled sampling fingers extend. This assures a particularly intensive cooling of the fingers.

Each of the finger is juxtaposed with a nozzle which can be opened or closed selectively to allow the sample to flow along the cold finger.

The coolant hose or pipe which is advantageously fixed to the center of the membrane which can correspond to the center of the sphere formed by the reservoir, has a length approximately equal to the radius of the sphere, thereby assuring a continued supply of the coolant to the bottom of the adsorber at which the fingers are mounted, in all positions of the unit as long as there is still liquid in the upper or first compartment and the pressure in this upper compartment, by evaporation of the coolant, remains greater than the ambient pressure to which the vaporized coolant from the heat exchange surface is vented.

The weighted-end flexible tube can be connected elsewhere on the membrane provided that it is of sufficient length to reach the lowest point in the upper or first compartment in all orientations of the vessel.

The position-dependent valve in the membrane allows liquid to pass unimpeded into the lower or second compartment and gas to be driven out of the latter in the normal or upright position of the vessel. However, when the vessel is tilted or inverted, the valve automatically closes and further flow is effected only through the flexible tube.

The valve also allows gas to be discharged when the liquid coolant is introduced into the vessel during startup. Additional venting ducts can also be provided for this purpose and can connect the upper portion of the lower or second compartment to the atmosphere.

The pressure-equalization tube which traverses the membrane and reaches substantially to the vertical axis of the upright device permits pressure equalization without significant transfer of the liquid from the lower compartment to the upper compartment when the unit is inverted or lies on its side.

The cryogenic adsorption unit is advantageously of cylindrical configuration and sealed in the opening of the bottom of the generally spherical coolant vessel. The heat exchanger surface can be a ring provided with a spiral passage for the coolant and connected to the flexible pipe mentioned previously at one end and via another tube through a venting valve to the atmosphere.

Juxtaposed with this ring is a removable flange cover which can be provided with the remote-controlled nozzles respectively aligned with the fingers. The fingers are advantageously removable and can be withdrawn by insertion of a vacuum gate or lock through the flange cover and can be carried by this lock to the ESR spectrometer.

The liquid reservoir is preferably provided with evacuated double-wall Dewar construction and advantageously between the walls hemispherical adjustable Teflon spacers are provided as described in the commonly assigned copending application Ser. No. 198,043 filed Oct. 17, 1980 and entitled "Wall Spacer for Double-Wall Vessels, Especially Dewar Flasks," now U.S. Pat. No. 4,343,413.

The cryogenic adsorber can consist of cylindrical copper sheets to which activated carbon has been bonded and which are composed of concentric cylinders. The adsorber unit is additionally supported with respect to the inner wall of the liquid reservoir by radial plates.

It has been found to be advantageous to mount the liquid reservoir in the vacuum vessel by means of wires under tension and to provide means for evacuating the space between the walls of the reservoir, either through a fitting which is generally cooled and can be provided with a position-dependent pressure relief valve. The evacuation of the vacuum vessel can be effected through a fitting in a valve with another pressure-burst membrane.

BRIEF DESCRIPTION OF THE DRAWING

The above and other objects, features and advantages of the present invention will become more readily apparent from the following description, reference being made to the accompanying drawing in which:

FIGS. 2a and 2b are detail axial sections of the inlet nozzle and the protective tube for the cooling finger shown in FIG. 2;

FIG. 3 is a bottom plan view of the lower flange cover of the device of FIG. 2;

FIG. 4a is an end view (seen in the direction of the nozzle) of a remotely controlled nozzle unblocking and blocking device in accordance with the invention;

FIG. 4b is a section generally along the line IVb—IVb of FIG. 4a;

FIG. 4c is a section generally along the line IVc—IVc of FIG. 4a with the closure frame in its erect position;

FIG. 4d is a sectional view taken in a plane perpendicular to the plane of FIG. 4c.

SPECIFIC DESCRIPTION

Figure 1:
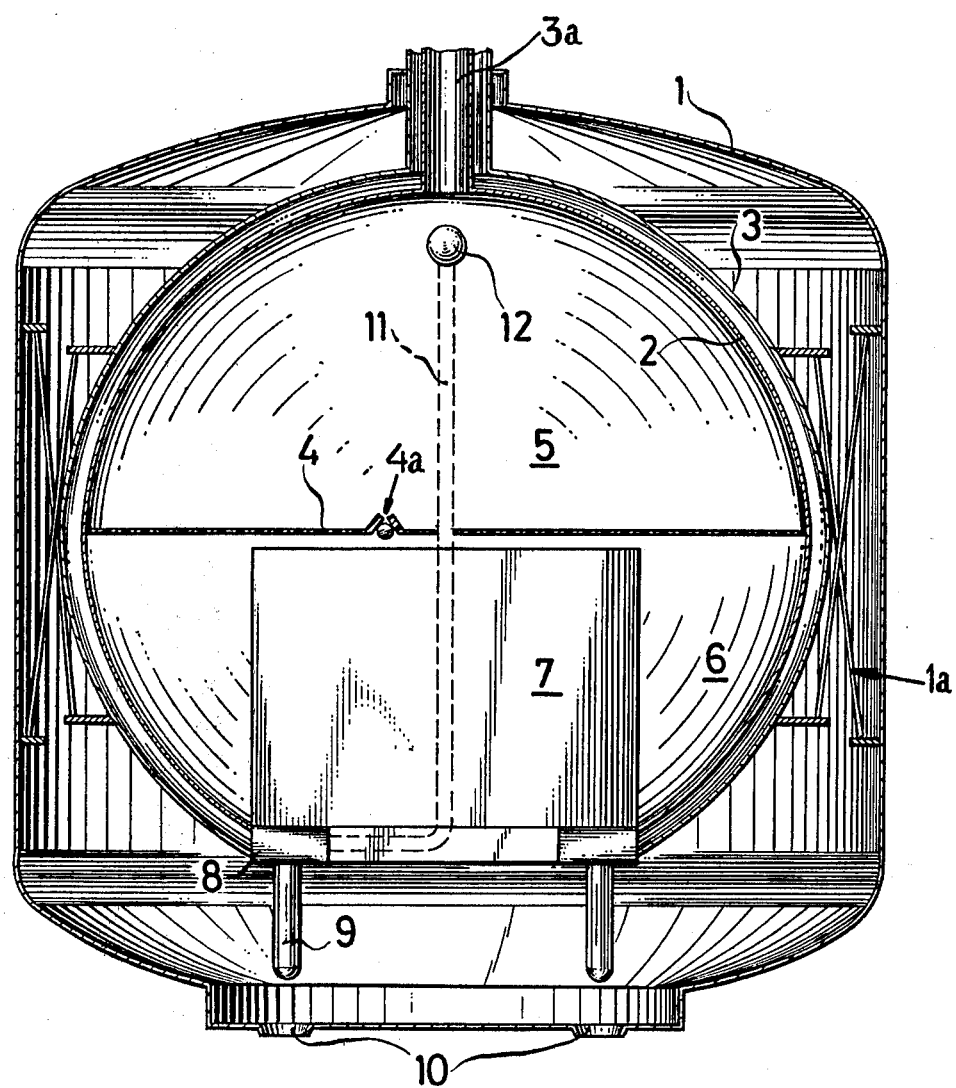
FIG. 1 is a somewhat schematic vertical section through a cryocollector according to the present invention, with parts shown in elevation, some parts being omitted to allow the principles of the invention to be more readily seen.

FIG. 1 shows some of the principal elements of a cryopump according to the invention. These elements include an evacuatable container or housing (vessel) 1 which can be composed of welded sheet metal and is dimensioned to sustain a high pressure gradient across the wall when the vessel is at ambient pressure, the external pressure being reduced as the vessel and the cryopump or cryocollector enclosed therein rises to considerable altitudes, e.g. up to 40 km, as carried by a balloon or the like.

The vessel 1 receives a liquefied coolant reservoir 2 in the form of a Dewar-type flask with a double-wall structure 3 having an evacuated compartment between silvered surfaces. The double wall 3 has a generally spherical configuration with a vertical neck 3a reaching upwardly through the housing 1.

The flask 2 is held in the vessel 1 by a shock-absorbing mount represented at 1a. This mount can consist of crossing tension strands connected between points on the flask and on the vessel and oriented to maintain the position of the flask relative to the vessel in spite of the transmission of shock to the system by, for example, acceleration and deceleration.

Figure 2:
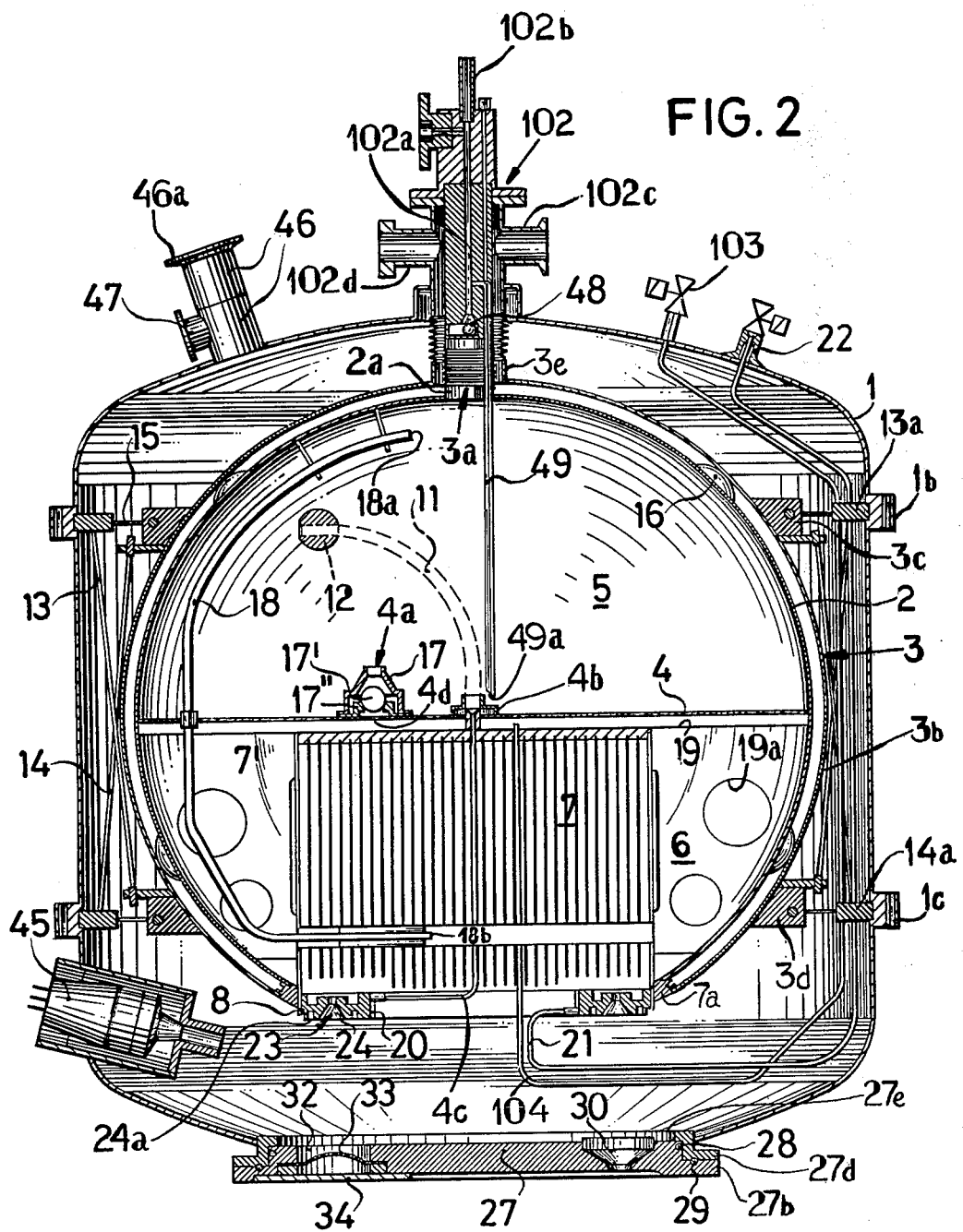
FIG. 2 is a similar cross section showing additional structural details of the cryocollector according to the invention.

The interior of the liquid coolant reservoir 2 is partitioned by a membrane 4 into an upper half 5 and a lower half 6, communication between these halves or compartments being effected through an orientationdependent valve 4a which has been represented only diagrammatically in FIG. 1 but is shown in greater detail in FIG. 2.

The lower half or compartment 6 of the reservoir includes a cryoadsorption unit 7. At the boundary between the cryoadsorption unit 7 and the liquid coolant reservoir 8 with cooling fingers 9 mounted therein, the cooling fingers being juxtaposed with nozzles 10 which can be provided in the bottom cover of the vessel 1.

The cooling or heating surfaces 8 are supplied with the liquid coolant from the upper half of the reservoir via a flexible conduit 11 whose free end carries a weight 12, the free end carrying this weight being continuously immersed in and supplied with liquid.

When the system of FIG. 1 is used for stratospheric air sampling, the cooling fingers 9 are fixed in the exchange surfaces 8 and the lower cover of the vessel 1 is closed, the cover being positioned so that the nozzles 10 are juxtaposed with the fingers 9. The interior of the vessel is then evacuated and the reservoir filled with the liquid coolant, usually liquid nitrogen. The liquid can be transferred from the upper half or compartment 5 to the lower half or compartment 6 through the valve 4a in the membrane 4 or by any other means, e.g. a conduit connecting the two compartments or a separate fitting communicating with the lower compartment and into which the liquid nitrogen is independently fed. The device is started and is lifted by the balloon to the stratospheric level at which sampling is of interest.

According to a predetermined program carried by the stratospheric probe and conventional control devices, or in accordance with a program controlled by a ground station, the nozzles 10 are opened and closed in succession at succeeding levels (see FIGS. 4a–4d).

Because of the vacuum in vessel 1, air from the respective level is drawn in through each nozzle 10 and flows along the respective cooling finger 9.

Carbon dioxide and other condensible substances in the air sample are frozen out of the sample (subliminated) on the cold finger while the remaining gases are picked up by the cryoadsorption unit 7 so that the reduced pressure in vessel 1 is sustained.

To cool the cold fingers 9, liquid nitrogen from the upper half of compartment 5 of the reservoir 2 is fed to the cooling surfaces 8 and thereafter can be vented from the vessel 1 directly. The weighted end of the flexible duct 11 always collects liquid coolant from the lowest point of the pool of this coolant in the upper half or compartment 5.

While the invention is represented in simplified form in FIG. 1, it is shown in greater detail in FIG. 2 and the other views which represent detail views thereof.

For example, the liquid reservoir 2, whose walls are spaced apart by insulating spacers 16 in the form of adjustable Teflon (polytetrafluoroethylene) hemispheres, can be mounted in the vacuum vessel 1 by tension wires 13, 14 and 15.

More particularly, the inner wall of the vessel 1 can be provided with a pair of rings 13a, 14a at which outer rings 1b and 1c are welded to the vessel to allow the parachute and balloons structure to be affixed to the sampling device.

The outer wall 3b of the double wall structure can carry a pair of rings 3c and 3d and radial tension wires 15 can connect each ring 3c or 3d with the ring 13a or 14a. In addition, the tension wires 13/14 can each be spanned between a respective ring 13a or 14a on the vessel 1 and a ring 3d or 3c on the reservoir 2. The neck 3a of the Dewar flask forming the reservoir 2 has an inner bellows member 2a communicating with the interior of the reservoir and an outer bellows member 3e to allow expansion and contraction movements with temperature change without rupture.

The spacers 16 can be oriented and constructed as described in the commonly assigned copending application Ser. No. 198,043 filed Oct. 17, 1980 and entitled "Wall Spacer For Double-Wall Vessels, Especially Dewar Flasks," now U.S. Pat. No. 4,343,413.

The membrane 4 which subdivides the two into the compartments 5 and 6, is provided with a fitting 4b at which the flexible tube 11 with its weighted end 12 is anchored and whereby this tube communicates via a rigid tube 4c with the heat exchanger or cooling surface 8 previously mentioned.

The membrane is also formed with the position-dependent valve 4a which, as illustrated, comprises an inner seat 17″ surrounding an orifice 4d in the membrane 4 and receiving a ball 17′ forming a check membrane of the valve. An outer frustoconical seat 17 surrounds the ball and seat 17″.

In the position shown valve 4a blocks flow from the upper compartment 5 to the lower compartment 6, the sampler being in its erect or normal orientation. However, when the sampler (vessel 1) is tilted or the device is inverted, the ball 17′ seats in membrane 17 to prevent flow from compartment 6 to compartment 5 but enabling flow of the liquid nitrogen from this compartment 5 to compartment 6.

A pressure-equalization tube 18 also traverses the membrane 4 and communicates via its end 18a with the upper portion of compartment 5 and with its end 18b with the lower portion of compartment 6. The lower end of this tube lies, in the indicated manner, substantially at the center of the lower portion of the lower reservoir compartment thereby preventing a flow of liquid from the lower part into the upper part when the unit lies on its side.

In the illustrated embodiment, the cryoadsorption unit 7 can be seen to be composed of concentric sheet metal (copper) cylinders to which activated carbon is bonded. This unit is sealed at its bottom, eg. by a ring 7a to the double wall 3 of the reservoir 2 and is supported by a plurality of radial plates 19 provided with openings 19a. The plates 19 are angularly equispaced about the cylindrical adsorption unit.

The line 4c carrying the liquid coolant through the adsorber, terminates in a spiral passage 20 on the cylindrical inner surface of the heat exchanger 8, the flow of the coolant through this spiral passage serving to cool the heat exchanger surfaces. Upon evaporation, the coolant is vented by a discharge conduit 21 with a vent valve 22 to the atmosphere directly.

The heat exchanger 8 is shown to be annular and to have receptacles 23 for a multiplicity of cooling fingers which are constructed as shown in FIG. 2a. The receptacle 23 is formed with a conical contact surface or seat 24 surrounded by a circular recess 24a which receives a boss of a protective tube 25 as will be described further below. The cooling finger can be held against the seat 24 by a nut.

As will be apparent from FIG. 2a, the cooling finger is formed with a conical upper end 9a dimensioned to fit snugly in the seat 24 and a flange 9b which serves to retain the protective shield tube 25 therein. This tube 25 has an internal thread 26 in which an internal nut 26a is threaded, this nut anchoring the cold finger on the ring 8, if desired. The cold finger 9 can be hollow so that coolant from the heat exchanger ring 8 can circulate therethrough or can simply be composed of a heat conductive metal which is chilled by conductive contact with the ring 8.

The flange cover 27 at the bottom end of the collector, is provided with a cylindrical boss 27a and an annular flange 27b. The cylindrical boss 27a receives an O-ring 28 in a circular peripheral groove to afford lateral sealing against the ring 27d.

The flange 27b is spaced from the flange 27d of the ring 27a surrounding the opening 27e by the balls 29 or ball bearings. Each of these balls can be set into blind recesses if desired. The bearings 29 form a rotatable connection between the flange 27 and the ring 27a even when the vessel 1 is evacuated. Brackets around the two flanges 27b and 27d (not shown) can prevent axial separation while allowing free rotation.

The cover 27 has eight angularly spaced openings 30 (see also FIG. 3) which are juxtaposed with respective cold fingers 9 and on which nozzles 31 can be fixed. The nozzle configuration is best shown in FIG. 4c.

As can be seen from FIG. 2b, each of the openings 30 has a frustoconical portion 30a converging toward a smaller frustoconical passage 30b and ultimately terminating in a cylindrical passage 30c surrounded by a circular groove 30d which receives an O-ring 31d (FIG. 4d) sealing the nozzle 31 to the flange 30. Four angularly equispaced threaded bores 30e are disposed outwardly of the groove 30d to receive bolts 31a which retain the nozzle 31 in place.

A further opening 32 (FIG. 2) is closed by a blow-out membrane 33 which is protected by a cover 34 (FIG. 3) against mechanical damage.

The inlet nozzles 31 are first unblocked and then blocked again by an opening and closure device more fully described in my commonly assigned copending application Ser. No. 198,130 filed Oct. 17, 1980 and entitled "Method and Apparatus for Remotely Controlling Orifice-Opening and Closing Operations".

This device has been shown in some detail in FIGS. 4a through 4d.

More particularly, a silicone-rubber disk 35 is recessed in the shank 35a of a T-shaped holder 35b whose cross bar 35c has bores 35d at its free extremities traversed by aluminum tie rods 35e. Member 35c thus forms a yoke.

Coil springs 37 surround the tie rods 35e and bear against opposite seats 37a and 37b, the latter resting against respective gas-tight explosive squibs 37c which can be of the type SKV 2/1 manufactured by DYNAMIT NOBEL AG and referred to as a Seil Kapp Vorrichtung. Upon firing of these squibs, therefore, the aluminum rods 35e will be severed and the compressed strings will drive the yoke 35c and the seal 35 away from the tip 31b of the orifice plate 31 to unblock the orifice. The firing of the squibs can be effected by receiver 100 carried by the balloon upon receipt of an appropriate signal from the ground or by an altitude-sensitive device carried by the balloon. The squibs are so-called Guillotinos having a sleeve provided with a bore through which the element to be severed extends. The element is cut by the firing of a charge which drives a blade through the element.

To close the orifice, we provide a frame 39 which includes another T-shaped yoke 38a whose shank 38b is fixed to a shaft 38c journaled in a block 38d mounted on the plate 27. A torsion spring 39 anchored at one end of this block and at its other end to the shaft 38c tends to swing the frame upwardly, i.e. in the counterclockwise sense as represented in FIG. 4d.

The frame is held in its recumbent position (FIG. 4a) by a stainless steel wire 38e unti a Guillotine squib 38f is fired by remote control or a unit on the balloon.

The frame 39 also includes a crossbar 38g in which plungers 38h and 40 are slidable, these plungers being urged downwardly (FIG. 4c) by respective coil springs 38k and 42.

At the end of plunger 40 there is provided a head 38m receiving a silicone disk 41 adapted to bear with the force of spring 42 against the boss 31c surrounding the orifice 31b.

A cam and indexing body 44 holds cam follower 43 away from the axis until the flank 44a of this cam is cleared by a cam follower head 43 on the plunger 38h. When the flank 44a is so cleared, the head 43 drops downwardly (arrow A in FIG. 4d) to index the frame in its erect position and allow the seal 41 to engage the orifice plate 31. The squib 38f can also be an SKV device.

The vessel 1 also contains measuring devices for pressure and temperature measurement. These devices can include a Thermothron tube 45 of the type produced by Leybold Company (Germany) and a resistance thermometer (not shown) connected to the heat exchanger ring 8.

The vessel 1 is also provided with a fitting 46 for evacuation and which can be closed by a plate 46a, the fitting having a branch 47 provided with a frangible membrane and cover such as has been shown at 33 and 34.

The upper fittings for the vessel 1 and the reservoir 2 can include a valve 48 which constitutes a position-dependent valve similar to the valve 4a and adapted to block escape of fluid.

The upper fitting 102 also includes a tube 49 which extends downwardly toward a free end 49a lying close to this membrane so that when the unit is turned on its head (upside down) to liquid nitrogen emerges although nitrogen gas can be vented.

The tube 49 opens into a passage 102a which is vented at 102b but which can be blocked if desired. The space between the walls of the reservoir 2 can be evacuated through fittings 102c and 102d. Another venting valve 103 is provided on the vessel 1 and communicates with a tube 104 which reaches upwardly through the lower compartment 6 to terminate just beneath the membrane.

The membrane or partition 4 in the coolant reservoir prevents an escape of the coolant in the upper compartment 5 during discharge of the previously cooled cryoadsorption unit 7 and also prevents transfer of the liquid coolant from the lower compartment 6 when the sample collector is tilted from its upright position or lies on its side or is inverted since the valve member 17' engages the seat 17 and seals the membrane. A pressure relief is then effected through the pressure equalization tube 18.

In the most undesirable case, with the unit lying exactly on its side so that its vertical axis as seen in FIG. 2 is exactly horizontal, about half of the coolant filling the lower compartment 6 will be able to run from the lower compartment to the upper compartment. This, however, does not interrupt the cooling of the fingers since coolant supply to the ring 8 is maintained by the weighted end of the flexible tube 11. The coolant which remains in the lower compartment maintains the functioning of the adsorber unit 7.

Figure 5:
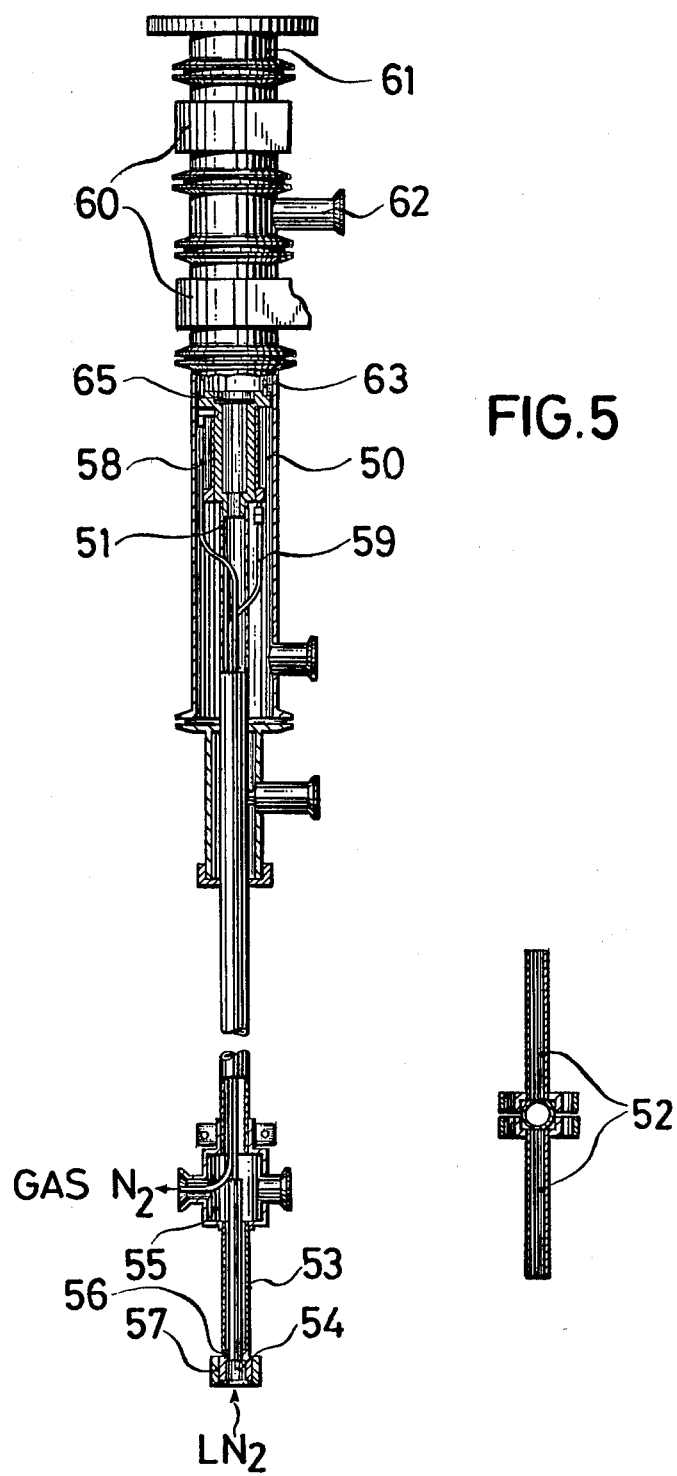
FIG. 5 is a partial section of a vacuum gate or lock arrangement for removal of the fingers or probes of FIG. 2.

The gate unit shown in FIG. 5 is used to discharge the collected samples into an ESR spectrometer.

In the receptacle portion of the gate shown in FIG. 5, there is provided a heat exchanger 50 which is fixed to a polished and hardened stainless steel pipe 51 which has two vacuum-tight compression threaded connections which via a pair of handgrippers 52 can be rotated and shifted. The heat exchanger 50 is provided with a Johnson coupling 53–57 and pipes 58, 59 for supplying the liquid coolant. The temperature of the heat exchanger can be determined by a thermistor (not shown) which is cemented in the heat exchanger.

The gate or lock has two gate valves or slide valves 60 and pipe sections 61 and 62 for connecting it in a vacuum-tight manner with the flange cover 27 upon removal of the cover 34 and the membrane 33. Alternatively, the membrane 33 can be left in place and can be ruptured by the vacuum applied through the gate or lock shown in FIG. 5 so that the latter can communicate in succession with the probe fingers for their removal. The cover 27 can be provided with three hand grips to facilitate its rotation.

The heat exchnager cools the gate or lock to about 77° K. and is then shifted over the finger 9 and rotated until the two pins 63 engage in corresponding openings in the nut 64. Contact between the heat exchanger and the finger is assured by a beryllium copper spring 65 which contacts the finger over the entire periphery of its cylindrical boss 64a. Upon rotation of the grip 52, the finger can be unscrewed and drawn into the gate tube. The slide valve 60 is then closed and the gate dismounted and connected at its lower end to a spectrometer. The materials collected on the finger 9 can be analyzed.

The device of the invention has significant advantages by comparison with conventional cryocollectors.

For example, while conventional devices for the purposes described cannot ensure cooling of the sample until landing, pickup and transfer to the spectrometer, so that samples could be lost and repetition of the experiment was necessary, the system of the invention guarantees retention of the sample and thus reduces personnel, equipment and operation cost.

Since an individual cooling system is used for each sample in conventional arrangements, weight limitations have limited the number of samplings per flight to about four. A single unit in accordance with the present invention may double this number of samples, thereby reducing the number of flights which may be required for a given number of samples by half.

Whereas conventional arrangements allow the sampling probe to contact the atmosphere during transfer to the ESR spectrometer, thereby reducing the quality of the determination, the arrangement of the present invention with its vacuum gate, eliminates all contact with the atmosphere.

Practically all earlier arrangements manifest considerable loss of the coolant with time, a significant problem when, after landing, the device must remain several hours before pickup or detection. Insulation is not always a solution since this can increase the weight and limit the effective size of the sampling device. Conventional systems either had to provide significant amounts of insulation or substantially higher quantities of liquid coolant by comparison with the device of the present invention.

In general, the pump capacity of the cryopump of the invention for the same adsorber volume is greater and regeneration of the adsorber without heating is possible.

We claim:
1. A cryostat comprising:
an evacuated vessel;
a reservoir for a cryogenic liquid coolant mounted in said vessel and having an upright normal position;
a membrane partitioning said reservoir into an upper first component and a lower second compartment in said position;
a cryogenic adsorber in said second compartment and communication with said vessel for maintaining a vacuum therein;
at least one cold surface disposed below said adsorber in said position;
means for cooling said surface and including at least one tube traversing said membrane and opening into said first compartment; and
a respective orifice formed on said vessel and selectively blockable and unblockable for passing material to be cooled to said cooled surface.

2. The cryostat defined in claim 1 wherein said tube extends from said membrane into said first compartment and is formed with a said free end therein adapted to reach low portions of said first compartment in all orientations of the sampler, said means for cooling further comprising a heat exchange ring, said surface being movably mounted on said ring.

3. The cryostat defined in claim 1 wherein said membrane is provided with a position-responsive valve communicating between said first and second compartments in said position and blocking communication between said compartments upon inversion of the cryostat.

4. The cryostat defined in claim 1, further comprising pressure-equalization means traversing said membrane and including a duct opening in said second compartment substantially at the axis thereof in said position.

5. The cryostat defined in claim 1 wherein said reservoir is generally spherical and is provided with an evacuated double-wall structure.

6. The cryostat defined in claim 5 wherein said adsorber comprises a plurality of concentric cylinders of copper sheet metal coated with activated carbon and is mounted in an opening formed in the bottom of said reservoir.

7. The cryostat defined in claim 6, further comprising radial support plates between an inner wall of said vessel and said adsorber.

8. The cryostat defined in claim 5, further comprising tension wires mounting said reservoir in said vessel.

9. The cryostat defined in claim 2 wherein said tube is fixed to said membrane substantially at the center thereof and has a length substantially equal to the radius of said reservoir, said reservoir being generally spherical.

10. The cryostat defined in claim 1 wherein said vessel is formed with a removable and rotatable flange plate juxtaposed with the bottom of said adsorber and provided with said orifices.

11. The cryostat defined in claim 10 wherein said flange plate is formed with an opening affording access to said surfaces, further comprising a vacuum lock insertable through said opening and engageable with said surfaces for removing same without exposure to said atmosphere.

12. The cryostat defined in claim 5 wherein each of said orifices is provided with a first closure element normally blocking the orifice and a second closure element, first triggerable means for dislodging said first element and second triggerable means for releasing said second element whereby said second element closes the respective nozzle.

* * * * *